United States Patent [19]

Franklin, Jr.

[11] Patent Number: 4,849,626
[45] Date of Patent: Jul. 18, 1989

[54] FIBER OPTIC BORE INSPECTION PROBE

[75] Inventor: Joseph O. Franklin, Jr., Lynchburg, Va.

[73] Assignee: The Babcock & Wilcox Company, New Orleans, La.

[21] Appl. No.: 120,297

[22] Filed: Nov. 13, 1987

[51] Int. Cl.$^4$ .......................... H01J 5/16; G01N 21/16
[52] U.S. Cl. ..................................... 250/227; 356/241
[58] Field of Search ...................... 356/241; 350/96.26, 350/96.25; 250/227

[56] References Cited

U.S. PATENT DOCUMENTS

| | | | |
|---|---|---|---|
| 3,494,354 | 2/1970 | Yokota et al. | 350/96.26 |
| 4,277,168 | 7/1981 | Oku | 356/241 |
| 4,281,929 | 8/1981 | Lord et al. | 356/241 |
| 4,634,857 | 1/1987 | Fey | 250/227 |
| 4,657,387 | 4/1987 | Heising et al. | 356/241 |
| 4,672,432 | 6/1987 | Casper | 356/241 |

FOREIGN PATENT DOCUMENTS 0938010  6/1982  U.S.S.R. ............................... 356/241

OTHER PUBLICATIONS

Kloots, "The Expanding World of Fiber Optics", *Optical Spectra*, 6/71, pp. 29-32.

Primary Examiner—David C. Nelms
Assistant Examiner—Michael Messinger
Attorney, Agent, or Firm—Vytas R. Matas; Robert J. Edwards

[57] ABSTRACT

A bore inspection probe utilizing optical fibers. A first layer of optical fibers and a second layer of optical fibers are placed over a tubular mandrel having a circular cross-section, and a mirror is placed adjacent the distal ends of the first and second optical fiber layers within the probe. The proximate ends of the optical fibers forming the second optical fiber layer are gathered into a bundle for exposure to a light source, whereas the proximate ends of the optical fibers forming the first optical fiber layer are fanned outwardly adjacent the end of the probe to form a thin optical fiber line. Light is transmitted to the surface of the bore via the second optical fiber layer and the mirror and is reflected from same via the mirror and the first optical fiber layer to form an image on the thin optical fiber line. Synchronization of a film with the movement of the probe within the bore produces a panoramic image of the surface of the bore on the thin optical fiber line.

6 Claims, 1 Drawing Sheet

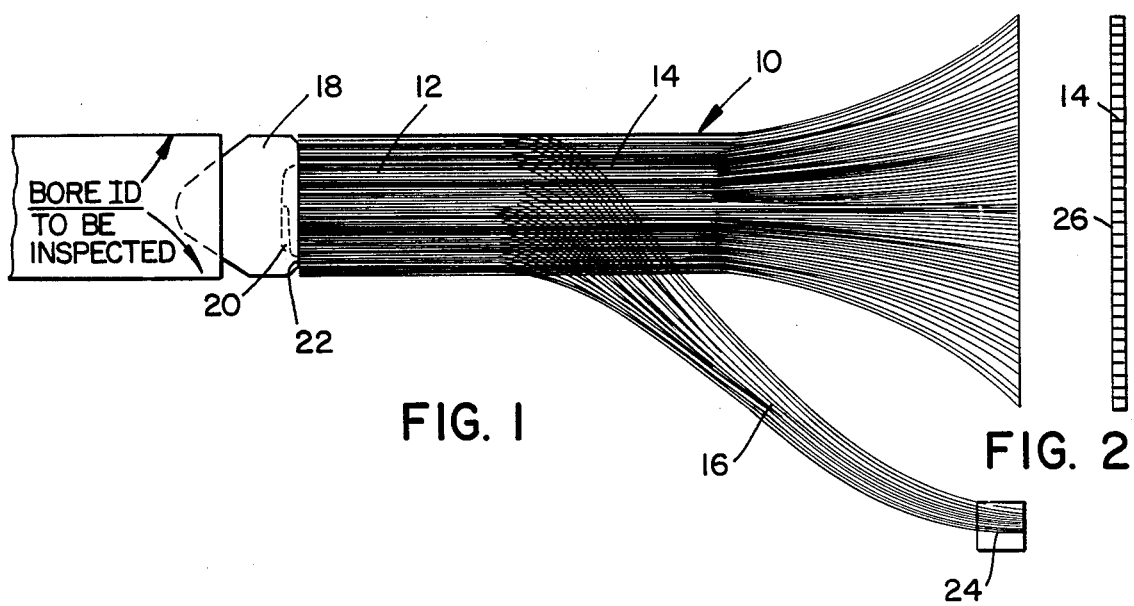
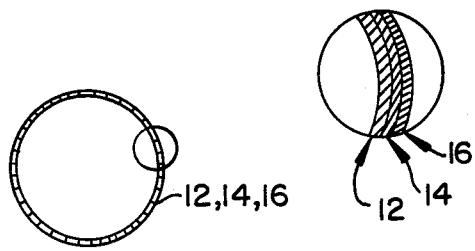
FIG. 1
FIG. 2
FIG. 3
FIG. 4

FIBER OPTIC BORE INSPECTION PROBE

TECHNICAL FIELD

The present invention relates to a probe for inspecting the surface of a bore and, more particularly, to a bore inspection probe that utilizes optical fibers for the transmission of incident light to and reflected light from the surface of a bore.

BACKGROUND ART

Presently, there is no known method for the complete interior inspection of the surface of a large diameter bore (greater than one inch in diameter) by optical fiber means. The only method currently available is to use a small diameter optical fiber bore scope and view small discrete areas of the surface of the bore as the field of view permits. This approach is impractical and produces unsatisfactory results since it is restricted by the field of view of the bore scope and there is also an additional problem of holding the focal distance of the scope when inspecting large diameter bores. Using a small diameter bore scope to inspect a large diameter bore has also proven to be very impractical due to the differences in diameters.

To overcome the foregoing problems, some laser scanning systems have become available for inspecting the surface of relatively large diameter bores. These systems can be used to locate reflective spots in the surface of the bore being inspected. Such reflective spots produce electrical impulses, but no permanent image is produced for record and review purposes.

Because of the foregoing limitations with respect to devices available for inspecting the surface of relatively large diameter bores and producing a record of any imperfections and/or discontinuities in same, it has become desirable to develop a fiber optic bore inspection probe that can be used for such inspection and produces a record of any imperfections and/or discontinuities in the bore surface.

SUMMARY OF THE INVENTION

The present invention solves the problems associated with the prior art and other problems by providing a bore inspection probe structure that utilizes optical fibers and can be employed to inspect the surface of relatively large diameter bores. The inspection probe is comprised of a round mandrel with two layers of optical fibers positioned axially along the outer circumference of the mandrel. The distal ends of the optical fibers are positioned so as to be in close proximity to a mirror which reflects any imperfections and/or discontinuities in the surface of the bore into the image transmitting optical fiber layer. The outer layer of optical fibers is used to transmit light from a light source to the surface of the bore. The inner layer of optical fibers is used to transmit an image of the surface of the bore as reflected by the mirror. The proximate ends of the light transmitting optical fibers, i.e., the outer layer of fibers, are gathered at the back end of the inspection probe into a random bundle which is received into a metal collar for substantially even exposure of the ends to the light source and to assist in heat dissipation from same. The proximate ends of the image transmitting layer of optical fibers, i.e., the inner layer of fibers, are fanned outwardly into a flat configuration so as to create a thin fiber line. This fiber line when presented to a film that is synchronized with the movement of the probe relative to the bore will produce a panoramic image of the surface of the bore as though the bore was split axially along its length and layed open into a flat configuration. Any imperfections and/or discontinuities in the surface of the bore will take on a light or dark shape against the background for inspection purposes. Identification numbers or letters can be photographed at the same time that the inspection probe is being inserted and/or being withdrawn from the bore or the numbers or letters can be inserted into the film electronically. In this manner, any imperfections and/or discontinuities in the surface of the bore can be located on the film and the film can serve as a permanent record of the inspection of the bore.

BRIEF DESCRIPTION OF THE DRAWINGS

FIG. 1 is a top plan view of the present invention.

FIG. 2 is a side elevational view of the present invention and illustrates the "fanning" outwardly of the image transmitting optical fiber layer to form a thin optical fiber line.

FIG. 3 is a cross-sectional view of the mandrel 12, and the first and second layers of optical fibers, 14, 16, respectively.

FIG. 4 is an enlarged partial cross-sectional view of FIG. 3 and illustrates the mandrel 12, the image transmitting layer of optical fibers 14 and the light transmitting layer of optical fibers 16.

DESCRIPTION OF THE PREFERRED EMBODIMENT

Referring now to FIG. 1, which is a top plan view of the fiber optic bore inspection probe 10 of the present invention, the overall configuration of the probe is tubular with a circular cross-section so as to be easily receivable in relatively large diameter bores to be inspected. As such, the inspection probe 10 includes a tubular mandrel 12 over which is placed a first layer 14 of optical fibers which acts as the image transmitting optical fiber layer and a second layer 16 of optical fibers which acts as the light transmitting optical fiber layer. The optical fibers in both the first optical fiber layer 14 and the second optical fiber layer 16 have a length which exceeds the length of the mandrel 12 and are positioned so as to be parallel to the longitudinal axis of the mandrel 12. The mandrel 12 has a cone shaped end 18 which acts as a guiding surface for centering the mandrel during insertion of the probe 10 into the bore to be investigated. Interposed between the distal ends 20 of the optical fiber layers 14 and 16 is a mirror 22 which transmits the images of the imperfections and/or discontinuities on the surface of the bore to the first layer 14 of optical fibers, i.e., the image transmitting optical fiber layer. The proximate ends of the second layer 16 of optical fibers, i.e., the light transmitting optical fiber layer, are gathered at the back end of the inspection probe 10 into a random bundle which is received into a metal collar 24 for substantially even exposure to a light source (not shown). The metal collar 24 also assists in dissipating heat produced by the light source. The proximate ends of the first layer 14 of optical fibers, i.e., the image transmitting optical fiber layer, is brought out of the back end of the probe and fanned outwardly into a flat configuration so as to create a thin fiber line 26. In this manner, a panoramic image of the surface of the bore as though it was split axially along its length and layed open into a flat configuration can be obtained.

Operationally, when the surface of a bore is to be inspected, the cone shaped end 18 of the inspection probe 10 is used as a guide surface for insertion of the probe into the bore. Prior to insertion, the light source is illuminated causing the second layer 16 of optical fibers, i.e., the light transmitting optical fiber layer, to transmit light therefrom to the surface of the bore via the mirror 22. Light reflected from the bore surface is transmitted via the mirror 22 through the first layer 14 of optical fibers to the end of the probe where the fibers are fanned outwardly into the fiber line 26. As the probe 10 is inserted into the bore and/or withdrawn from same, the thin fiber line 26 produces a panoramic image of the inside surface of the bore to a film that is synchronized with the relative movement of the probe within the bore. Any imperfections and/or discontinuities in the inner surface of the bore will take on a light or dark shape against a background. These light or dark shapes appear on the thin fiber line 26 which can then be photographed by the film that is synchronized with the movement of the probe 10. Identification numbers or letters can also be photographed at the same time the probe 10 is being inserted into or being withdrawn from the bore or can be placed on the film electronically. In this manner, any imperfections and/or discontinuities in the surface of the bore can be located on the film and the film can act as a permanent record of the inspection of the bore.

Certain modifications and improvements will occur to those skilled in the art upon reading the foregoing. It should be understood that all such modifications and improvements have been deleted herein for the sake of conciseness and readability, but are properly within the scope of the following claims.

I claim:

1. A probe for inspecting the surface of a bore, comprising:
   a mandrel having a substantially circular cross section;
   a first layer of optical fibers placed axially on the circumference of said mandrel and;
   a second layer of optical fibers axially received over said first optical fiber layer, said first and second optical fiber layers each having a distal end within said probe adjacent to a mirror for transmitting light from one of said optical fiber layers to the surface of the bore, the other of said optical fiber layers receiving light reflected from the surface of the bore, and transmitting said received light to a proximate end, said proximate end being formed outwardly to form an optical fiber line.

2. The probe as defined in claim 1 wherein said second optical fiber layer has a proximate end outside of the probe and adjacent to a light source allowing light from the light source to be transmitted from said proximate end of said second optical fiber layer to said distal end of said second optical fiber layer.

3. The probe as defined in claim 2, further including a collar receiving said proximate end of said second optical fiber layer.

4. The probe as defined in claim 1 further including a cone shaped tip positioned adjacent to an end of said mandrel within the probe to form a guiding surface for same, said distal ends of said first and second optical fiber layers being adjacent to said cone shaped tip on said mandrel.

5. The probe as defined in claim 1 wherein said first optical fiber layer is oriented so as to be substantially parallel to a longitudinal axis of said mandrel.

6. The probe as defined in claim 1 wherein said second optical fiber layer is oriented so as to be substantially parallel to a longitudinal axis of said mandrel.

* * * * *